United States Patent
Cheng et al.

(10) Patent No.: US 7,671,241 B2
(45) Date of Patent: Mar. 2, 2010

(54) HOST MATERIAL FOR BLUE OLED AND WHITE LIGHT EMITTING DEVICE UTILIZING THE SAME

(75) Inventors: Chien-Hong Cheng, Hsin-Chu (TW); Jin-Ju Lin, Taichung County (TW)

(73) Assignee: National Tsing Hua University, Hsinchu (TW)

( * ) Notice: Subject to any disclaimer, the term of this patent is extended or adjusted under 35 U.S.C. 154(b) by 262 days.

(21) Appl. No.: 12/000,147

(22) Filed: Dec. 10, 2007

(65) Prior Publication Data

US 2009/0062570 A1    Mar. 5, 2009

(30) Foreign Application Priority Data

Aug. 28, 2007    (TW) ............................... 96131802 A

(51) Int. Cl.
C07C 43/205 (2006.01)
C07C 25/18 (2006.01)
C07C 15/12 (2006.01)
H01L 27/32 (2006.01)

(52) U.S. Cl. .................. 568/633; 570/129; 570/183; 585/400; 313/504; 257/79; 428/690

(58) Field of Classification Search .......... None
See application file for complete search history.

(56) References Cited

U.S. PATENT DOCUMENTS

2005/0236977 A1* 10/2005 Yamada et al. .............. 313/504
2007/0270595 A1* 11/2007 Kim et al. ................... 548/469
2009/0200919 A1* 8/2009 Kamatani et al. ........... 313/504

\* cited by examiner

*Primary Examiner*—Rosalynd Keys
(74) *Attorney, Agent, or Firm*—Muncy, Geissler, Olds & Lowe, PLLC

(57) ABSTRACT

The invention provides a host material for organic light emitting diodes, having the general formula:

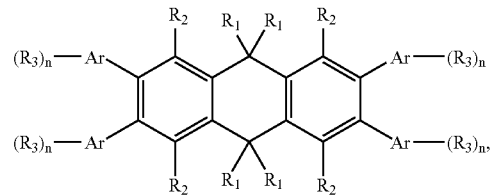

wherein $R_1$ is selected from a $C_{1-8}$ alkyl group, each $R_2$ is independently selected from a hydrogen or a $C_{1-8}$ alkyl group, Ar is selected from a $C_{5-14}$ aromatic or hetero aromatic group, $R_3$ is selected from a $C_{5-14}$ aromatic or hetero aromatic group, a $C_{1-8}$ alkyl group, a $C_{5-8}$ cycloalkyl group, a $C_{1-8}$ fluoroalkyl group, or a $C_{1-8}$ alkoxyl group, and n is an integer of 1-10. The host materials have a higher energy gap (greater than 4.0 eV), and high thermal stability.

15 Claims, 8 Drawing Sheets

HOST MATERIAL FOR BLUE OLED AND WHITE LIGHT EMITTING DEVICE UTILIZING THE SAME

BACKGROUND OF THE INVENTION

1. Field of the Invention

The invention relates to an organic light emitting diode (OLED), and in particular to a host material in a light emitting layer of the OLED.

2. Description of the Related Art

Phosphate metal complexes have been utilized as dopants in OLED. Because of strong spin orbital coupling, the cyclo-metallated iridium complexes draw the most attention in this field. The triplet state lifetime of the iridium complexes is reduced by hybridization of the siglet and triplet states, thereby enhancing its quantum yield. In addition, the device efficiency can be improved by doping the phosphate materials into host materials. Therefore, the host materials have gradually become major research topics. In recent papers, the host materials for blue phosphate have revealed problems such as insufficient energy gap and low thermal stability due to small molecular weight. Please see *Nature* (London) 1998, 395, 151 by Baldo et al., *J. Appl. Phys.* 2001, 90, 4058 by Adachi et al., *J. Org. Chem.* 1976, 41, 3682 by Granoth et al., *Appl. Phys. Lett.* 2003, 83, 3818 by Holmes et al., and *J. Org. Chem.* 1976, 41, 3682 by Granoth et al.

SUMMARY OF THE INVENTION

The invention provides a host material utilized in an organic light emitting diodes having the general formula:

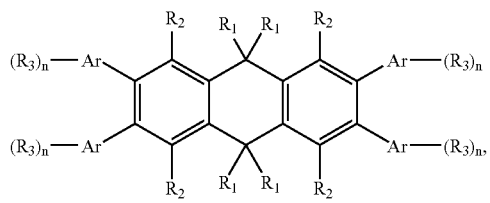

wherein $R_1$ is selected from a $C_{1-8}$ alkyl group, each $R_2$ is independently selected from a hydrogen or a $C_{1-8}$ alkyl group, Ar is selected from a $C_{5-14}$ aromatic or hetero aromatic group, $R_3$ is selected from a $C_{5-14}$ aromatic or hetero aromatic group, a $C_{1-8}$ alkyl group, a $C_{5-8}$ cycloalkyl group, a $C_{1-8}$ fluoroalkyl group, or a $C_{1-8}$ alkoxyl group, and n is an integer of 1-10.

The invention also provides a blue OLED, comprising an anode, a hole transporting layer on the anode, an electron blocking layer on the hole transport layer, a light emitting layer on the electron blocking layer, a hole blocking layer on the light emitting layer, an electron transporting layer on the hole blocking layer, and a cathode, wherein the light emitting layer comprises the host material as described above and a dopant.

The invention further provides a white light emitting device, comprising the blue OLED as described above, a red OLED; and a green OLED.

A detailed description is given in the following embodiments with reference to the accompanying drawings.

BRIEF DESCRIPTION OF THE DRAWINGS

The invention can be more fully understood by reading the subsequent detailed description and examples with references made to the accompanying drawings, wherein.

DETAILED DESCRIPTION OF THE INVENTION

The following description is of the best-contemplated mode of carrying out the invention. This description is made for the purpose of illustrating the general principles of the invention and should not be taken in a limiting sense. The scope of the invention is best determined by reference to the appended claims.

The invention provides a blue OLED and a host material utilized in a light emitting layer of the blue OLED. The host material has large energy gap, greater than 4.0 eV, and high thermal stability. Therefore, the blue OLED utilizing the host material has high brightness, high quantum yield, high current efficiency, and an excellent CIE coordinate.

The described host material has a general formula as Formula 1:

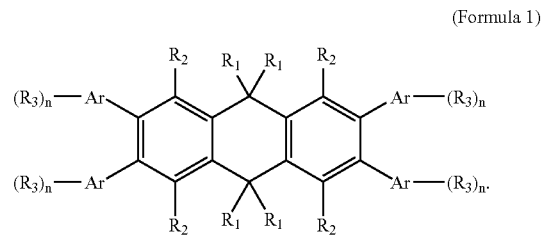

(Formula 1)

In Formula 1, $R_1$ is selected from a $C_{1-8}$ alkyl group, each $R_2$ is independently selected from a hydrogen or $C_{1-8}$ alkyl group, Ar is selected from a $C_{5-14}$ aromatic or hetero aromatic group, $R_3$ is selected from a $C_{5-14}$ aromatic or hetero aromatic group, a $C_{1-8}$ alkyl group, a $C_{5-8}$ cycloalkyl group, a $C_{1-8}$ fluoroalkyl group, or a $C_{1-8}$ alkoxyl group, and n is an integer of 1-10.

The synthesis of the host material is described below. As shown in Formula 2, the anthracene with different substituent $R_2$ is alkylated by bis(2-alkoxyethyl)ether and lithium aluminum hydride (LAH) to form 9,9,10,10-tetralkyl-9,10-dihydro-anthracene. In Formula 2, $R_1$ is selected from a $C_{1-8}$ alkyl group and each $R_2$ is independently selected from hydrogen or electron donating groups such as a $C_{1-8}$ alkyl group.

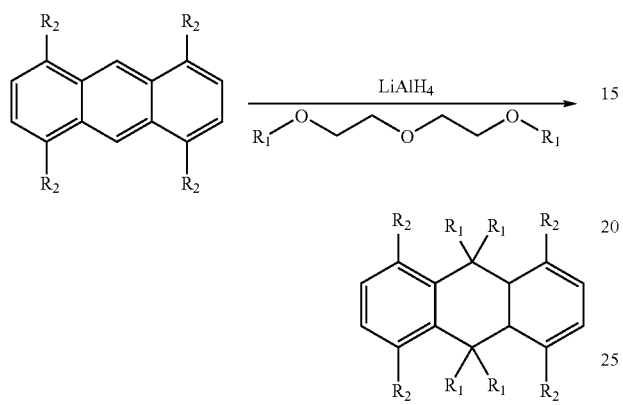

(Formula 2)

Subsequently, the described 9,9,10,10-tetralkyl-9,10-dihydro-anthracene is brominated to form 2,3,6,7-tetrabromo-9,9,10,10-tetralkyl-9,10-dihydro-anthracene, as shown in Formula 3.

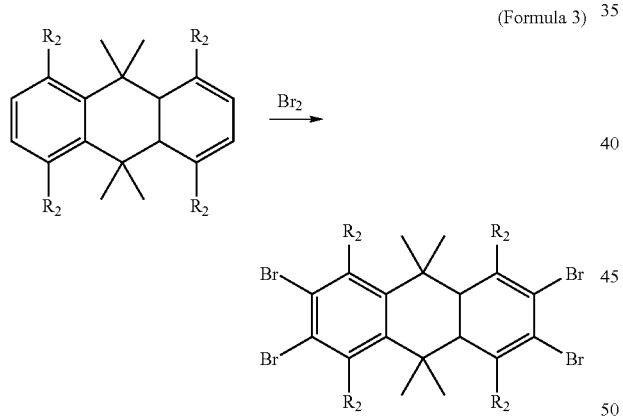

(Formula 3)

At last, the 2,3,6,7-tetrabromo-9,9,10,10-tetralkyl-9,10-dihydro-anthracene is reacted with an arylboronic acid to form 2,3,6,7-tetraryl-9,9,10,10-tetralkyl-9,10-dihydro-anthracene by so-called Suzuki coupling, as shown in Formula 4. In Formula 4, Ar can be $C_{5-14}$ aromatic groups as phenyl, naphthalenyl, anthracenyl, or phenanthrenyl groups, or heteroaromatic groups as furanyl, pyrrolyl, thiophenyl, thiazolyl, imidazolyl, pyranyl, pyridinyl, imidinyl, indolyl, purinyl, or carbazolyl groups. $R_3$ are substituents on Ar, including a $C_{5-14}$ aromatic or hetero aromatic group, a $C_{1-8}$ alkyl group, a $C_{5-8}$ cycloalkyl group, a $C_{1-8}$ fluoroalkyl group, or a $C_{1-8}$ alkoxyl group. n is substituent number on Ar, an integer of 1-10.

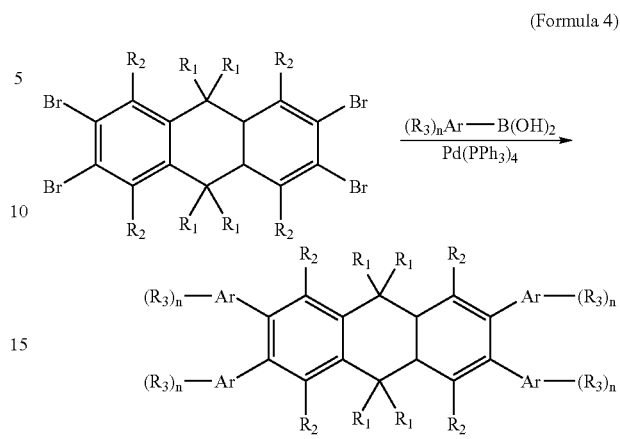

(Formula 4)

Figure 1:
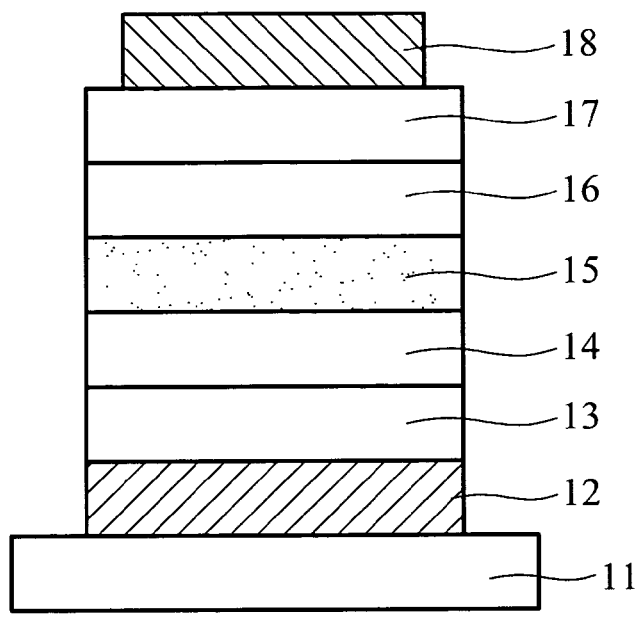
FIG. 1 is a cross section of an OLED structure in one embodiment of the invention.

2,3,6,7-tetraryl-9,9,10,10-tetralkyl-9,10-dihydro-anthracene in Formula 1 can be host material of the light emitting layer of a blue OLED. In one embodiment, OLED is a multi-layered structure as shown in FIG. 1. The formation method, is to first form an anode 12 on a glass substrate 11, wash the anode 12 by a wet etching or plasma process, evaporate or spin coat a hole transfer layer (HTL) 13 on the anode 12, evaporate or spin coat an electron blocking layer (EBL) 14 on the HTL 13, evaporate or spin coat a light emitting layer 15 on the EBL 14, evaporate or spin coat a hole blocking layer (HBL) 16 on the light emitting layer 15, evaporate or spin coat an electron transfer layer (ETL) 17 on the HBL 16, and finally vacuum coat a cathode 18 on the ETL 17 to complete the blue OLED of one embodiment.

The anode 12 has a thickness of about 80 nm, including indium tin oxide (hereinafter ITO), indium zinc oxide (hereinafter IZO), aluminum zinc oxide (hereinafter AZO), cadmium tin oxide (hereinafter CTO), tin oxide ($SnO_2$), zinc oxide (ZnO), or other transparent conductive materials.

The HTL 13 has a thickness of about 30 nm to 50 nm, including N,N'-bis(1-naphthalenyl)-N,N'=diphenyl-1,1'-biphenyl-4,4-diamine (hereinafter NPB), N,N-diphenyl-N,N-bis(3-methylphenyl)-1,1-biphenyl-4,4-diamine (hereinafter TPD), (4'-carbozol-9-yl-biphenyl-4-yl-naphthalen-1-yl-phenyl-amine (hereinafter NCB), N,N'-di-phenanthren-9-yl-4,N'-diphenyl-biphenyl-4,4'-diamine (hereinafter PPB), bis(4-N,N'-diethylamino-2-methylphenyl)-4-methylphenyl methane (hereinafter MPMP), 3,3'-dimethyl-N,N,N',N'-tetra-m-tolyl-biphenyl-4,4'-diamine (hereinafter HMTPD), Tris(4-carbazol-9-yl-phenyl)amine (hereinafter TCTA), or other suitable arylamine.

EBL 14 has a thickness of about 20 nm to 30 nm, including N,N'-dicarbazolyl-3,5-benzene (hereinafter mCP), 4,4'-N,N'-dicarbazole-biphenyl (hereinafter CBP), 1,4-dicarbazol-9-yl-benzene (hereinafter CCP), or 1,3,5-tris(N-carbazolyl)benzene (hereinafter TCB).

The light emitting layer 15 has a thickness of about 30 nm to 40 nm, the host material thereof is 2,3,6,7-tetraryl-9,9,10,10-tetralkyl-9,10-dihydro-anthracene in Formula 1, and the dopant thereof can be complex of osmium (Os), iridium (Ir), platinum (Pt), Europium (Eu), ruthenium (Ru), and the likes. The iridium complex has superior quantum yield and illumination wavelength range, and ligand of the complex is nitrogen-containing heterocyclic compound. In one embodiment, the iridium complex can be iridium(III) bis [(4,6-difluorophenyl)-pyridinato-N,C2']-5-(pyridine-2-yl)-1H-triazolate (hereinafter Firpytz), iridium(III) bis[(4,6-difluorophenyl)- pyridinato-N,C']picolinate (hereinafter Firpic), iridium(III) bis[(4,6-difluorophenyl)-pyridinato-N,C']-5-(pyridine-2-yl)-1H-tetrazolate (hereinafter FIrN4), iridium(III) bis[(4,6-difluorophenyl)-pyridinato-N,C']tetrakis(1-pyrazoyl)borate (hereinafter FIr6), or iridium(III) tris(1-phenyl-3-methyl-benzoimidazolin-2-ylidene-C,C') (hereinafter Ir(pmb)$_3$). The host material and the dopant have a volume ratio of about 95:5 to 90:10.

The HBL 16 has a thickness of about 10 nm to 15 nm, including 1,3,5-tris(phenyl-2-benzimidazolyl)-benzene (hereinafter TPBI), 2,9-dimethyl-4,7-diphenyl-1,10-phenanthroline (hereinafter BCP), aluminium(III) bis(2-methyl-8-quninolinato)-4-phenylphenolate, hereinafter BAlq, aluminium(III) bis(2-methyl-8-quninolinato)-phenolate (hereinafter PAlq), aluminium(III) bis(2-methyl-8-quninolinato)-triphenylsilanyloxy (hereinafter SAlq, or 1,4-bis(triphenylsilyl benzene (hereinafter UGH2).

The ETL has a thickness of about 30 nm to 50 nm, including TPBI, 4-naphthalen-1-yl-3,5-diphenyl-4-[1,2,4]triazole (hereinafter TAZ-1), 3,4,5-triphenyl-4-[1,2,4]triazole (hereinafter TAZ-2), 3-biphenyl-4-yl-5-(4-tert-butyl-phenyl)-4-phenyl-4-[1,2,4]triazole (hereinafter TAZ-3), 2-biphenyl-4-yl-5-(4-tert-butyl-phenyl)-[1,3,4]oxadiazole (hereinafter PBD), tris(8-hydroxyquinoline) aluminum (hereinafter Alq$_3$), or 4,7-diphenyl-[1,10]phenanthroline (hereinafter DPA).

The cathode 18 has a thickness of about 50 nm to 100 nm, including magnesium-aluminum alloy, magnesium-silver alloy, magnesium-indium alloy, aluminum-lithium alloy, lithium fluoride, or aluminum.

Figure 2:
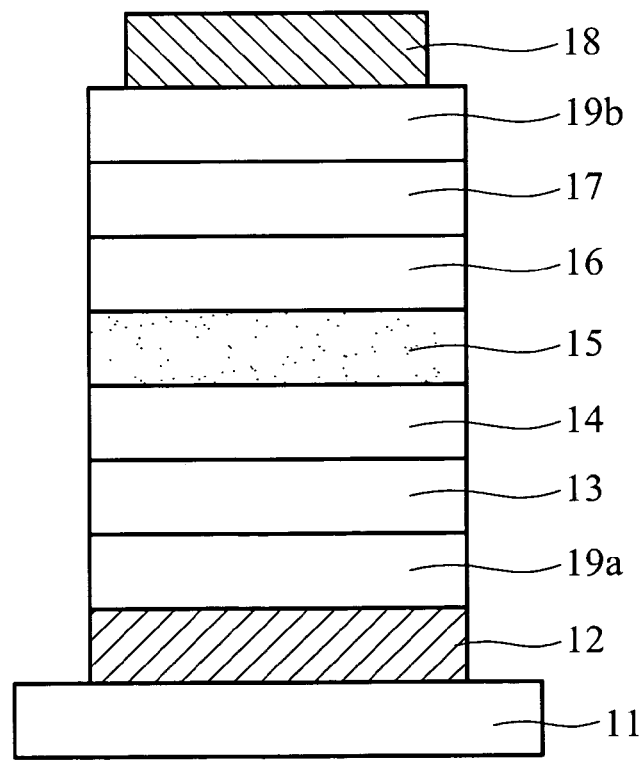
FIG. 2 is a cross section of an OLED structure in one embodiment of the invention.

In addition, the described blue OLED may further include a hole injection layer (hereinafter HIL) and an electron injection layer (hereinafter EIL) as shown in FIG. 2. The HIL 19a is disposed between the anode 12 and the HTL13, having a thickness of about 5 nm to 20 nm. The HIL 19a can be arylamine, porphyrin derivatives, or p-doped amine derivatives. The aryamine includes 4,4',4"-tris(3-methylphenylphenylamino)triphenylamine (hereinafter m-MTDATA), 4,4',4"-tris[2-naphthyl(phenyl)amino]triphenylamine (hereinafter 2-TNATA), or other suitable arylamine. The porphyrin derivatives can be copper phthalocyanine (hereinafter CuPc). The EIL 19b is disposed between the cathode 18 and the ETL 17, having a thickness of about 0.5 nm to 5 nm. The EIL 19b can be alkali metal halides, alkaline earth metal halides, alkali metal oxide, or metal carbonate, such as lithium fluoride (LiF), cesium fluoride (CsF), sodium fluoride (NaF), calcium fluoride (CaF$_2$), lithium oxide (Li$_2$O), cesium oxide (Cs$_2$O), sodium oxide (Na$_2$O), lithium carbonate (Li$_2$CO$_3$), cesium carbonate (Cs$_2$CO$_3$), or sodium carbonate (Na$_2$CO$_3$).

The described blue OLED may collocate with other known red and green OLEDs to form a white light emitting device.

Figure 3:
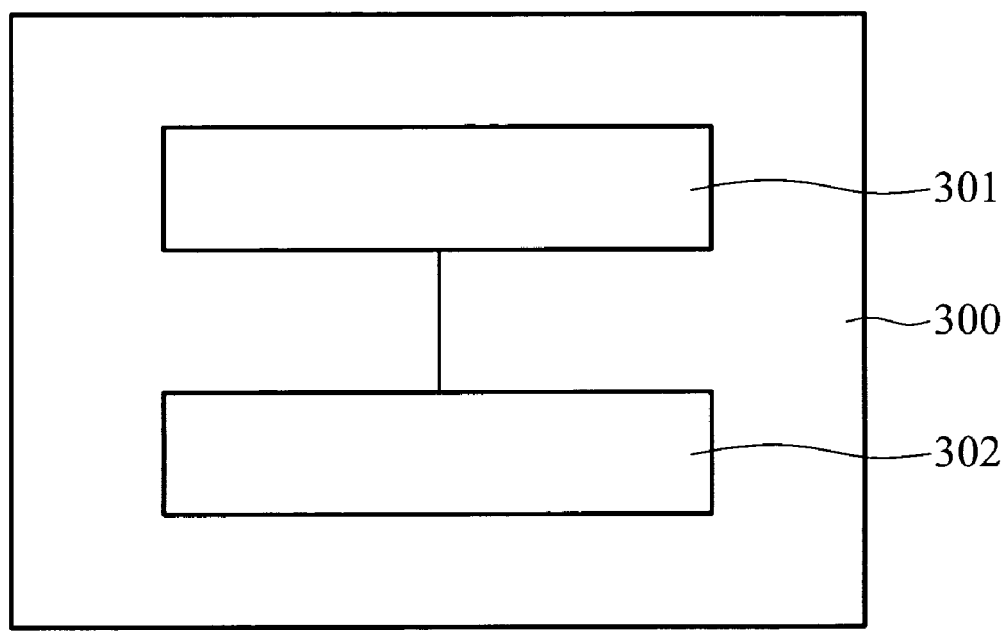
FIG. 3 is a diagram showing a display device utilizing the OLED of the invention.

As shown in FIG. 3, the invention can be applied in a display device 300. The display device includes the described blue OLED 301, a driving circuit 302 coupling to the blue OLED 301 to drive it. The driving circuit includes a passive matrix or an active matrix thin film transistor (TFT). If the driving circuit further couples to red and green OLEDs and drives them, a so-called full color display device is finished.

EXAMPLE 1

The Synthesis of 9,9,10,10-tetramethyl-9,10-dihydro-anthracene 10 mmol of anthracene was charged in a reaction vessel, 10 mL of bis(2-methoxyethyl)ether and 26 mmol of LAH were then added to the vessel, and the mixture was heated to reflux under nitrogen for 6 hours. The reaction was then cooled to room temperature, added 4N HCl solution in ice bath to quench reaction, and then filtered to get white solid (9,9,10,10-tetramethyl-9,10-dihydro-anthracene) with 70% yield. The reaction was shown in Formula 5, and the product had spectra as below. $^1$H NMR (400 MHz, CDCl$_3$, ppm): δ7.50-7.52 (m, 4H), 7.23-7.25 (m, 4H), 1.66 (s, 12H).

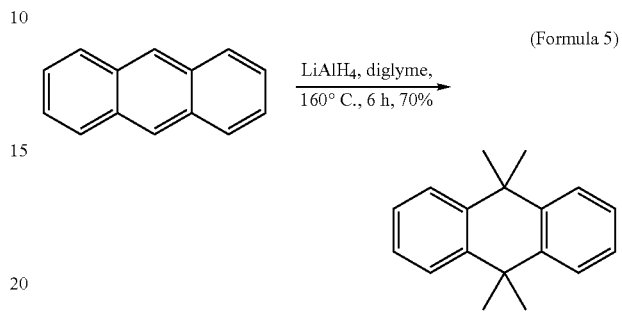

(Formula 5)

EXAMPLE 2

The Synthesis of 2,3,6,7-tetrabromo-9,9,10,10-tetramethyl-9,10-dihydro-anthracene The product of Example 1 (10 mmol) was charged in a reaction vessel and 100 mL of dichloromethane was added to dissolve it. In another reaction vessel, bromine water was added to 50 mL of dichloromethane. These two solutions were mixed by a double-ended needle, and then reacted at ice bath for 1 hour. After the reaction, large amount of distillation water was added to quench the reaction, and 100 mL of dichloromethane was added for extraction. The organic layer of the extraction was washed by saturated sodium thiosulphate solution and saturated salt water, and dried by anhydrous magnesium sulphate. Most of the solvent of the organic layer was removed by a rotavapor, and the solid in the residue solvent was collected by filtering. The solid was then washed by few ethyl ether to obtain a pale yellow product (2,3,6,7-tetrabromo-9,9,10,10-tetramethyl-9,10-dihydro-anthracene) with 81% yield. The reaction was shown in Formula 6, and the product had spectra as below. $^1$H NMR (600 M Hz, CDCl$_3$): δ 1.57 (s, 12 H), 7.65 (s, 4 H). $^{13}$C NMR (150 M Hz, CDCl$_3$): δ 34.7 (CH$_3$), 37.1(C), 122.6 (C), 131.9 (CH), 142.3 (C).

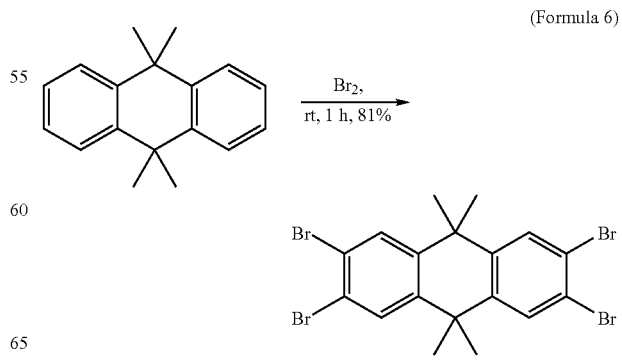

(Formula 6)

EXAMPLE 3

Figure 4:
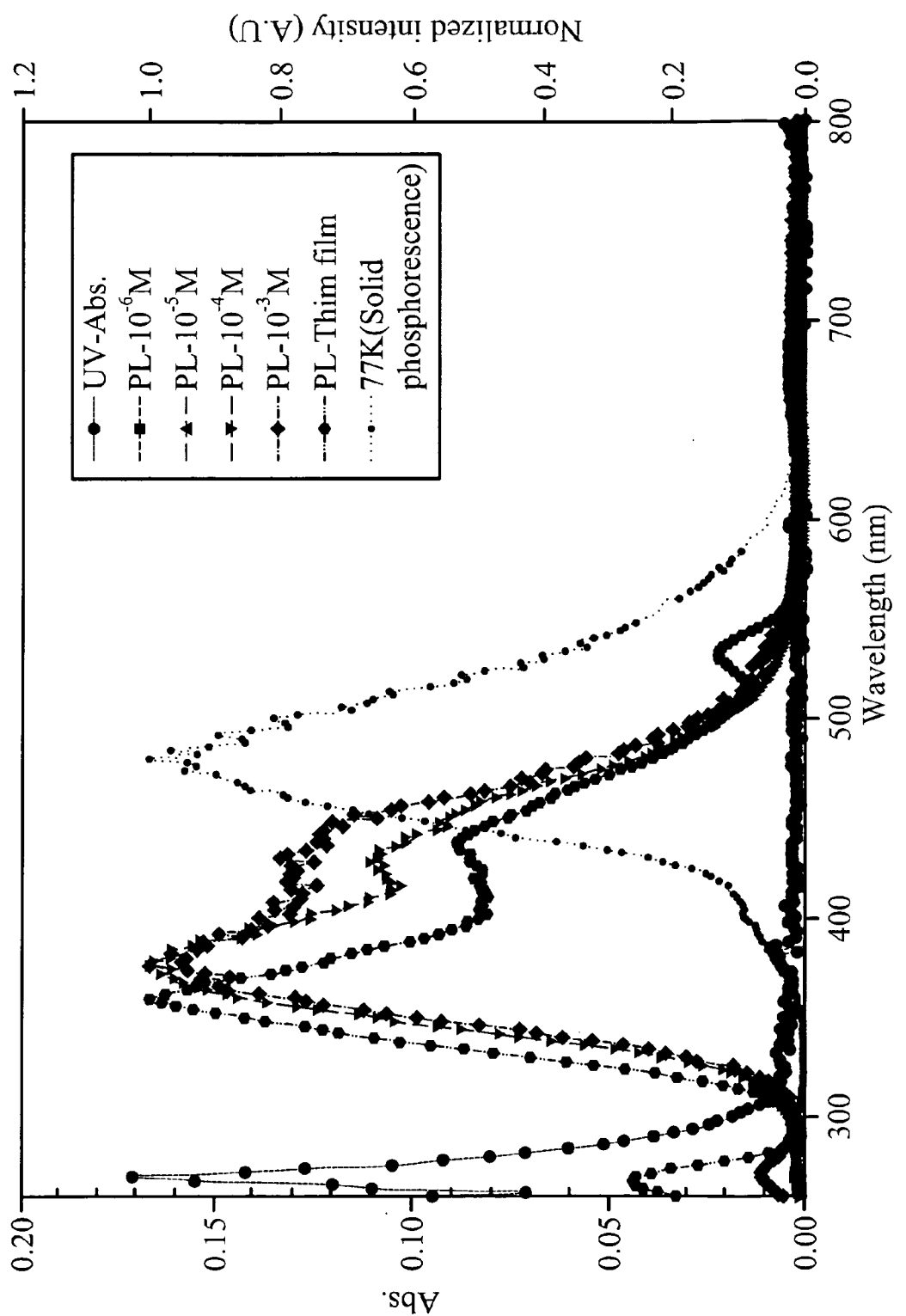
FIG. 4 shows UV-VIS absorption and photo luminescent spectra of the TTA-tBu in a dichloromethane solution and thin film type, and solid phosphorescence emission spectra at 77K of the TTA-tBu.

Synthesis of 2,3,6,7-Tetrakis-(4-tert-butyl-phenyl)-9,9,10,10-tetramethyl-9,10-dihydro-anthracene 10 mmol of product in Example 2, 40 mmol of 4-tert-butylphenylboronic acid, and 0.2 mmol of Pd(PPh$_3$)$_4$ were charged in a reaction vessel under nitrogen. The mixture was added deoxygen benzene (50 mL), ethanol (4 mL), and 2M potassium carbonate solution (10 mL) to be dissolved, and then heated to 80° C. and reacted for 24 hours. The reaction result was extracted by 50 mL of ethyl acetate to obtain an organic layer. The organic layer was filtered through diatomite and dried by anhydrous magnesium sulphate. Most of the solvent of the dried organic layer was removed to obtain a solid. The solid was subsequently washed by distillation water, methanol, ethyl ether to obtain 2,3,6,7-Tetrakis-(4-tert-butyl-phenyl)-9,9,10,10-tetramethyl-9,10-dihydro-anthracene (hereinafter TTA-tBu). The Suzuki coupling was shown in Formula 7, and the product had spectra as below. $^1$H NMR (400 M Hz, CDCl$_3$): δ 1.31 (s, 36 H), 1.79 (s, 12 H), 7.12 (d, 8 H, J=8.4 Hz), 7.24 (d, 8 H, J=8.4 Hz), 7.55 (s, 4 H). $^{13}$C NMR (100 M Hz, CDCl$_3$): δ 31.4 (CH$_3$), 34.4(C), 35.1 (CH$_3$), 37.1 (C), 124.6 (CH), 128.9 (CH), 129.5 (CH), 138.3 (C), 138.8 (C), 141.0 (C), 149.1 (C). HRMS (FAB, m/z): calcd for C$_{58}$H$_{68}$ 764.5321, found 765.5397 (M+H$^+$). Anal. Calcd. for C$_{58}$H$_{68}$: C, 91.04; H, 8.96%. Found: C, 91.07; H, 8.90%. FIG. 4 shows UV-VIS absorption and photo luminescent spectra of the TTA-tBu in a dichloromethane solution and thin film type, and solid phosphorescence emission spectra at 77K of the TTA-tBu.

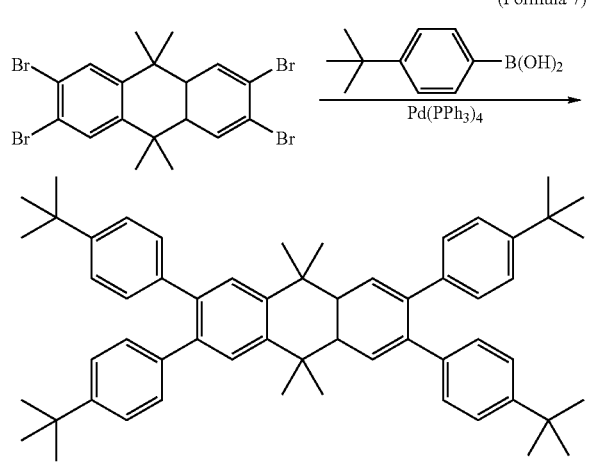

(Formula 7)

EXAMPLE 4

Figure 5:
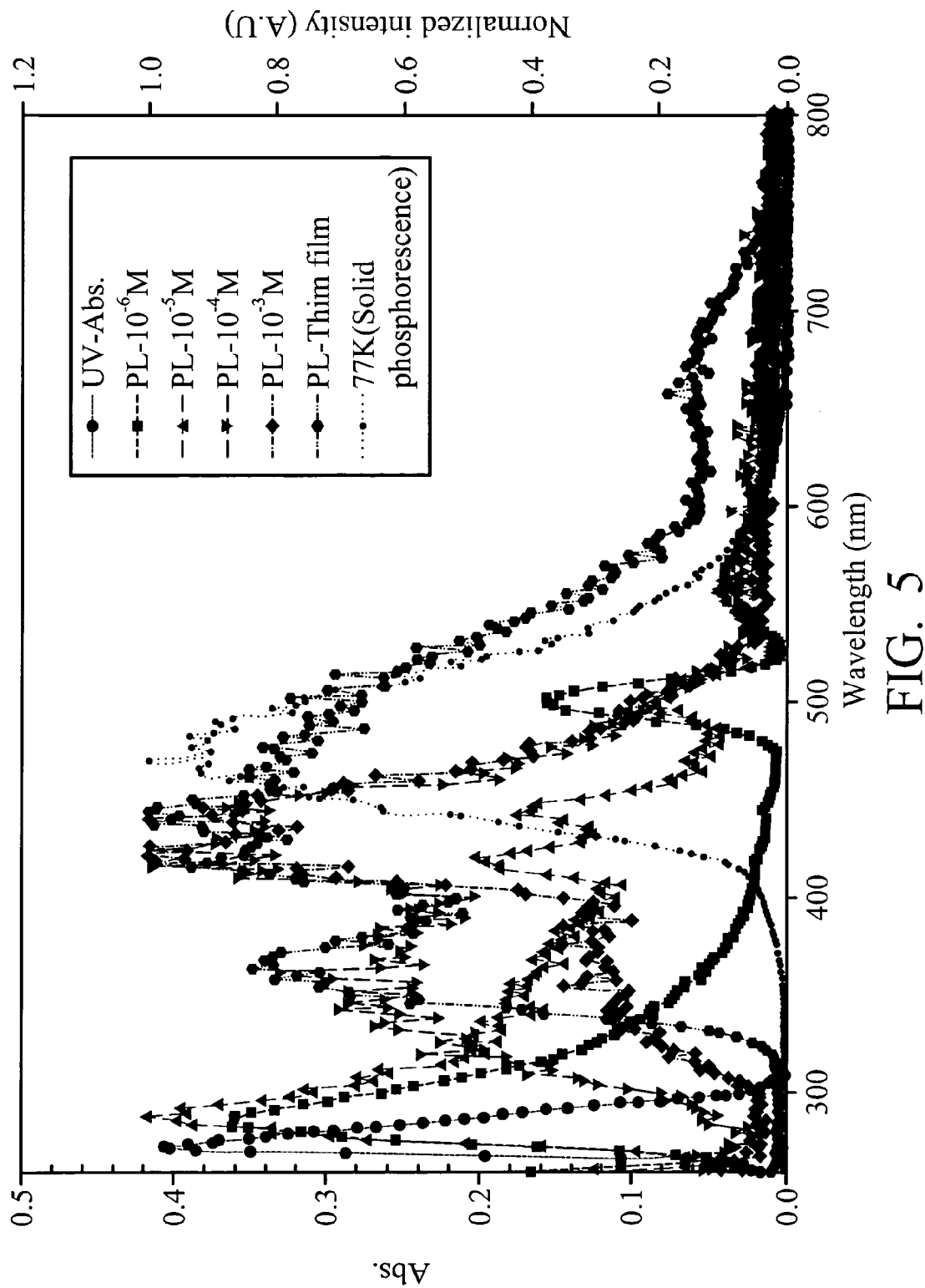
FIG. 5 shows UV-VIS absorption and photo luminescent spectra of the TTA-$CF_3$ in a dichloromethane solution and thin film type, and solid phosphorescence emission spectra at 77K of the TTA-$CF_3$.

Synthesis of 2,3,6,7-Tetrakis-(3,5-bis-trifluoromethyl-phenyl)-9,9,10,10-tetramethyl-9,10-dihydro-anthracene Similar to Example 3, the only difference was that the 4-tert-butylphenylboronic acid in Example 3 was replaced with 3,5-bis(trifluoromethyl)-phenylboronic acid, while other reaction reagents, steps, and conditions were the same. The product of Example 4 has a formula as shown in Formula 8, named 2,3,6,7-Tetrakis-(3,5-bis-trifluoromethyl-phenyl)-9,9,10,10-tetramethyl-9,10-dihydro-anthracene (hereinafter TTA-CF$_3$). TTA-CF$_3$ had a specta as below. $^1$H NMR (400 M Hz, CDCl$_3$): δ 1.88 (s, 12 H), 7.58 (s, 8 H), 7.69 (s, 4 H), 7.79 (s, 4 H). $^{13}$C NMR (100 M Hz, CDCl$_3$): δ 35.1 (CH$_3$), 37.6 (C), 120.9 (CH), 123.0 (C, q, J$_{C-F}$=270 Hz), 128.8 (CH), 129.9 (CH), 131.9 (C, q, J$_{C-F}$=34 Hz), 136.3 (C), 142.3 (C), 142.9 (C). HRMS (FAB, m/z): calcd for C$_{50}$H$_{28}$F$_{24}$ 1084.1808, found 1085.1886 (M+H$^+$). Anal. Calcd. for C$_{50}$H$_{28}$F$_{24}$: C, 55.36; H, 2.60%. Found: C, 55.18; H, 2.74%. FIG. 5 shows UV-VIS absorption and photo luminescent spectra of the TTA-CF$_3$ in a dichloromethane solution and thin film type, and solid phosphorescence emission spectra at 77K of the TTA-CF$_3$.

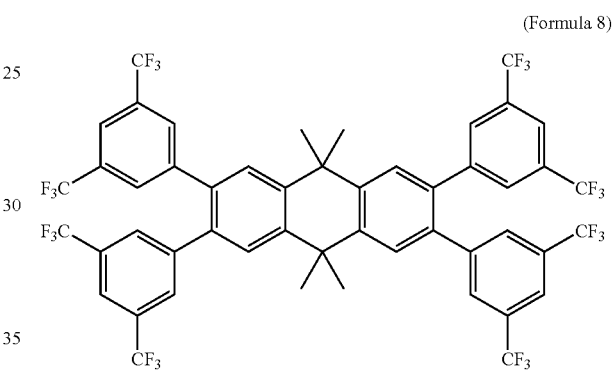

(Formula 8)

EXAMPLE 5

Figure 6:
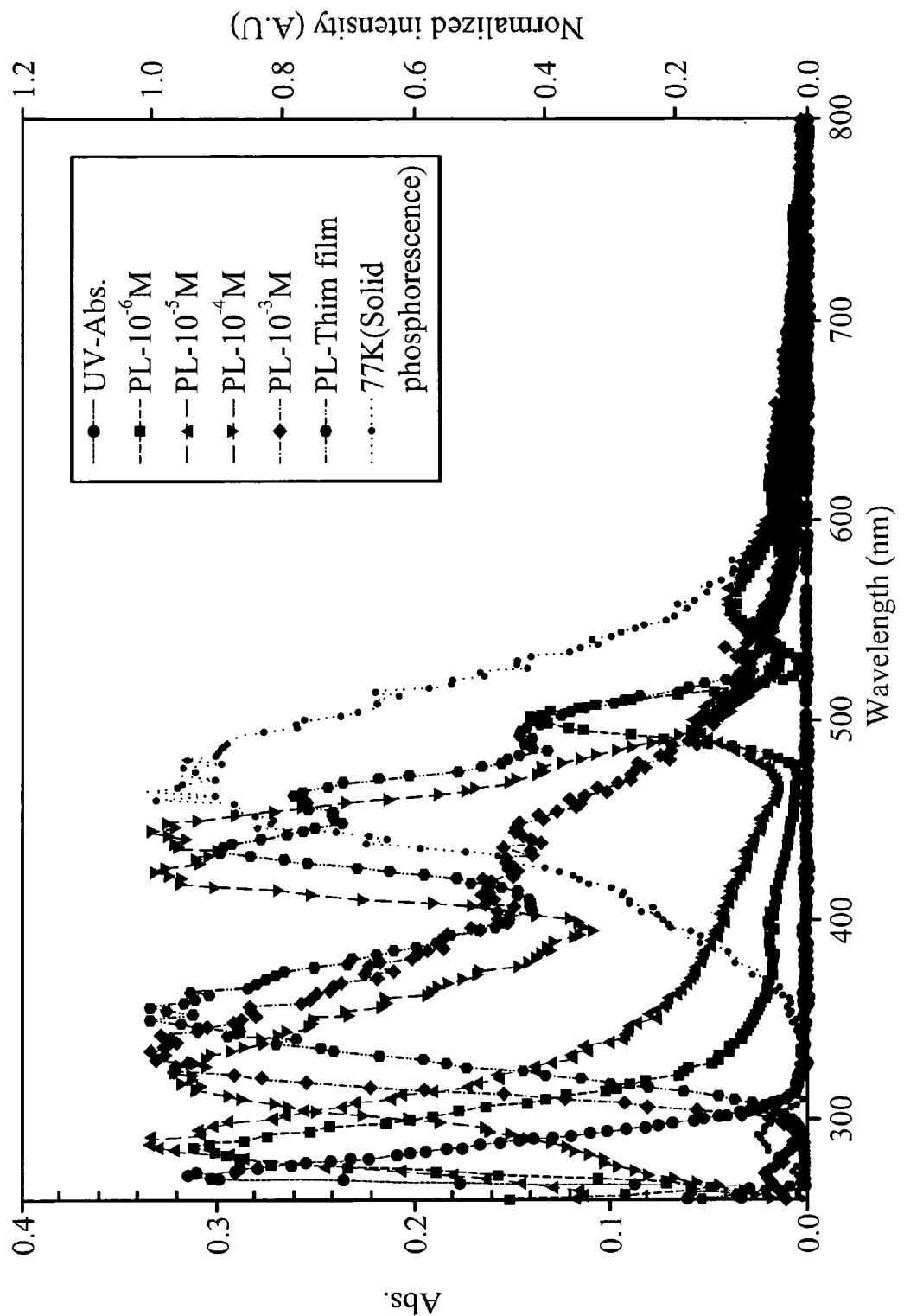
FIG. 6 shows UV-VIS absorption and photo luminescent spectra of the TTA-Me in a dichloromethane solution and thin film type, and solid phosphorescence emission spectra at 77K of the TTA-Me.

Synthesis of 2,3,6,7-Tetrakis-(3,5-dimethyl-phenyl)-9,9,10,10-tetramethyl-9,10-dihydro-anthracene Similar to Example 3, the only difference was that the 4-tert-butylphenylboronic acid in Example 3 was replaced with 3,5-dimethyl-phenylboronic acid, while other reaction reagents, steps, and conditions were the same. The product of Example 5 has a formula as shown in Formula 9, named 2,3,6,7-Tetrakis-(3,5-dimethyl-phenyl)-9,9,10,10-tetramethyl-9,10-dihydro-anthracene (hereinafter TTA-Me). TTA-Me had a specta as below. $^1$H NMR (400 M Hz, CDCl$_3$): δ 1.78 (s, 12 H), 2.21 (s, 24 H), 6.79 (s, 8 H), 6.83 (s, 4 H), 7.52 (s, 4 H). $^{13}$C NMR (150 M Hz, CDCl$_3$): δ 21.3 (CH$_3$), 35.1 (CH$_3$), 37.0 (C), 127.7 (CH), 127.8 (CH), 128.7 (CH), 136.9 (C), 138.4 (C), 140.9 (C), 141.5 (C). HRMS (EI, m/z): calcd for C$_{50}$H$_{52}$ 652.4069, found 652.4072 (M$^+$). Anal. Calcd. for C$_{50}$H$_{52}$: C, 91.97; H, 8.03%. Found: C, 92.03; H, 8.05%. FIG. 6 shows UV-VIS absorption and photo luminescent spectra of the TTA-Me in a dichloromethane solution and thin film type, and solid phosphorescence emission spectra at 77K of the TTA-Me.

(Formula 9)

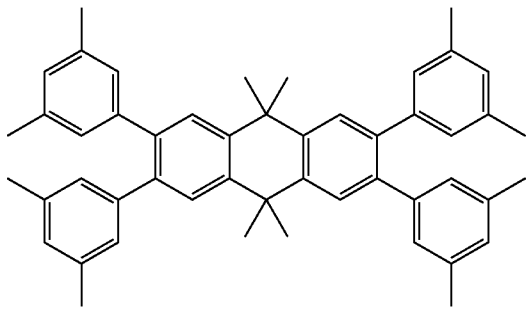

EXAMPLE 6

Figure 7:
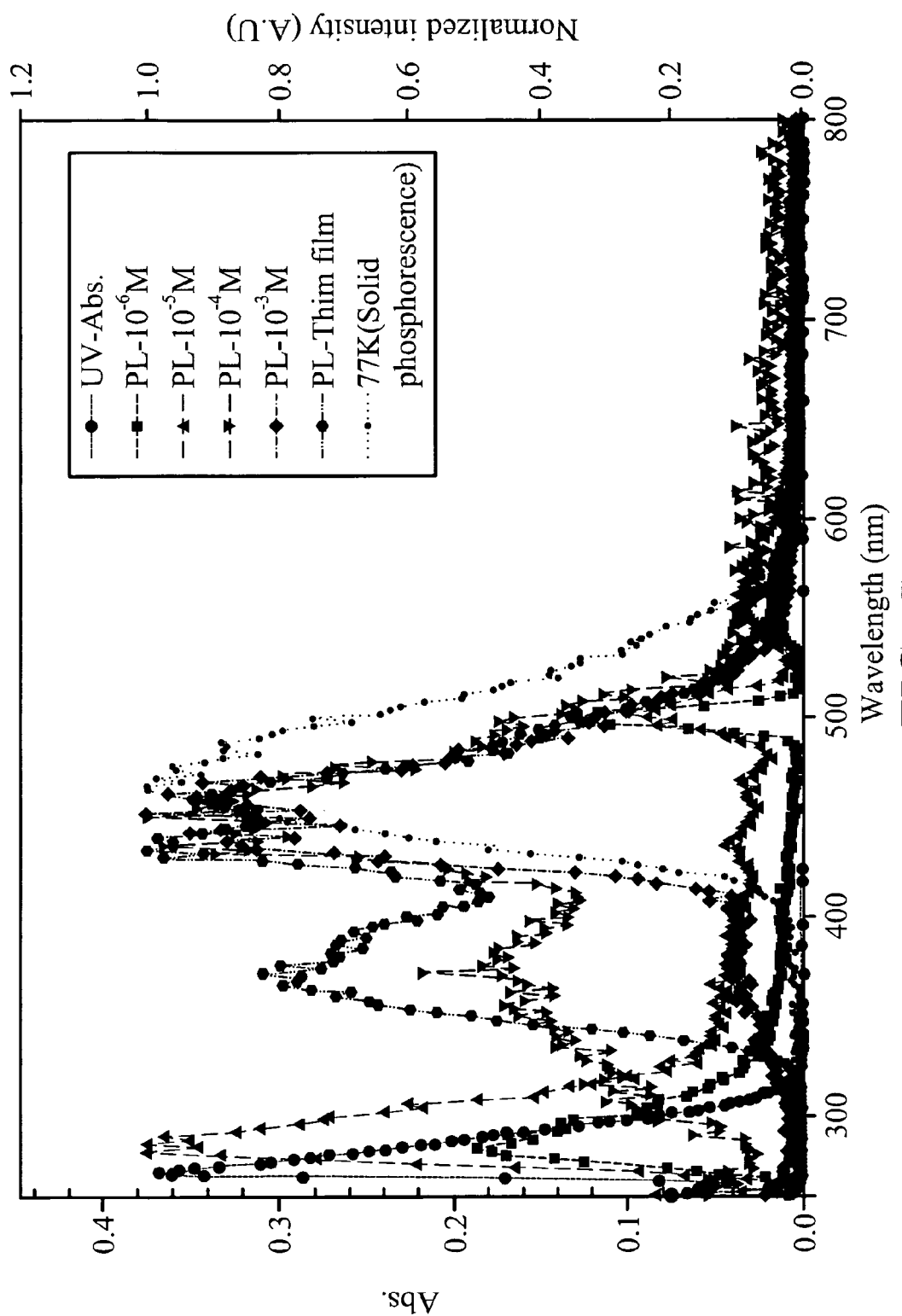
FIG. 7 shows UV-VIS absorption and photo luminescent spectra of the TTA-OMe in a dichloromethane solution and thin film type, and solid phosphorescence emission spectra at 77K of the TTA-OMe.

Synthesis of 2,3,6,7-Tetrakis-(3,5-dimethoxy-phenyl)-9,9,10,10-tetramethyl-9,10-dihydro-anthracene Similar to Example 3, the only difference was that the 4-tert-butylphenylboronic acid in Example 3 was replaced with 3,5-dimethoxy-phenylboronic acid, while other reaction reagents, steps, and conditions were the same. The product of Example 6 has a formula as shown in Formula 10, named 2,3,6,7-Tetrakis-(3,5-dimethoxy-phenyl)-9,9,10,10-tetramethyl-9,10-dihydro-anthracene (hereinafter TTA-OMe). TTA-OMe had a specta as below. $^1$H NMR (400 M Hz, CDCl$_3$): δ 1.78 (s, 12 H), 3.63 (s, 24 H), 6.34 (t, 4 H, J=2 Hz), 6.39 (d, 8 H, J=2 Hz), 7.57 (s, 4 H). $^{13}$C NMR (100 M Hz, CDCl$_3$): δ 35.1 (CH$_3$), 37.1 (C), 55.3 (CH$_3$), 98.9 (CH), 107.9 (CH), 128.5 (CH), 138.3 (C), 141.2 (C), 143.6 (C), 160.2 (C). HRMS (EI, m/z): calcd for C$_{50}$H$_{52}$O$_8$ 780.3662, found 780.3637 (M$^+$). Anal. Calcd. for C$_{50}$H$_{52}$O$_8$: C, 76.90; H, 6.71%. Found: C, 77.02; H, 6.43%. FIG. 7 shows UV-VIS absorption and photo luminescent spectra of the TTA-OMe in a dichloromethane solution and thin film type, and solid phosphorescence emission spectra at 77K of the TTA-OMe.

(Formula 10)

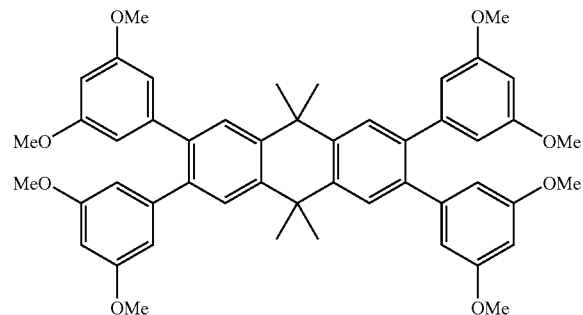

EXAMPLE 7

Figure 8:
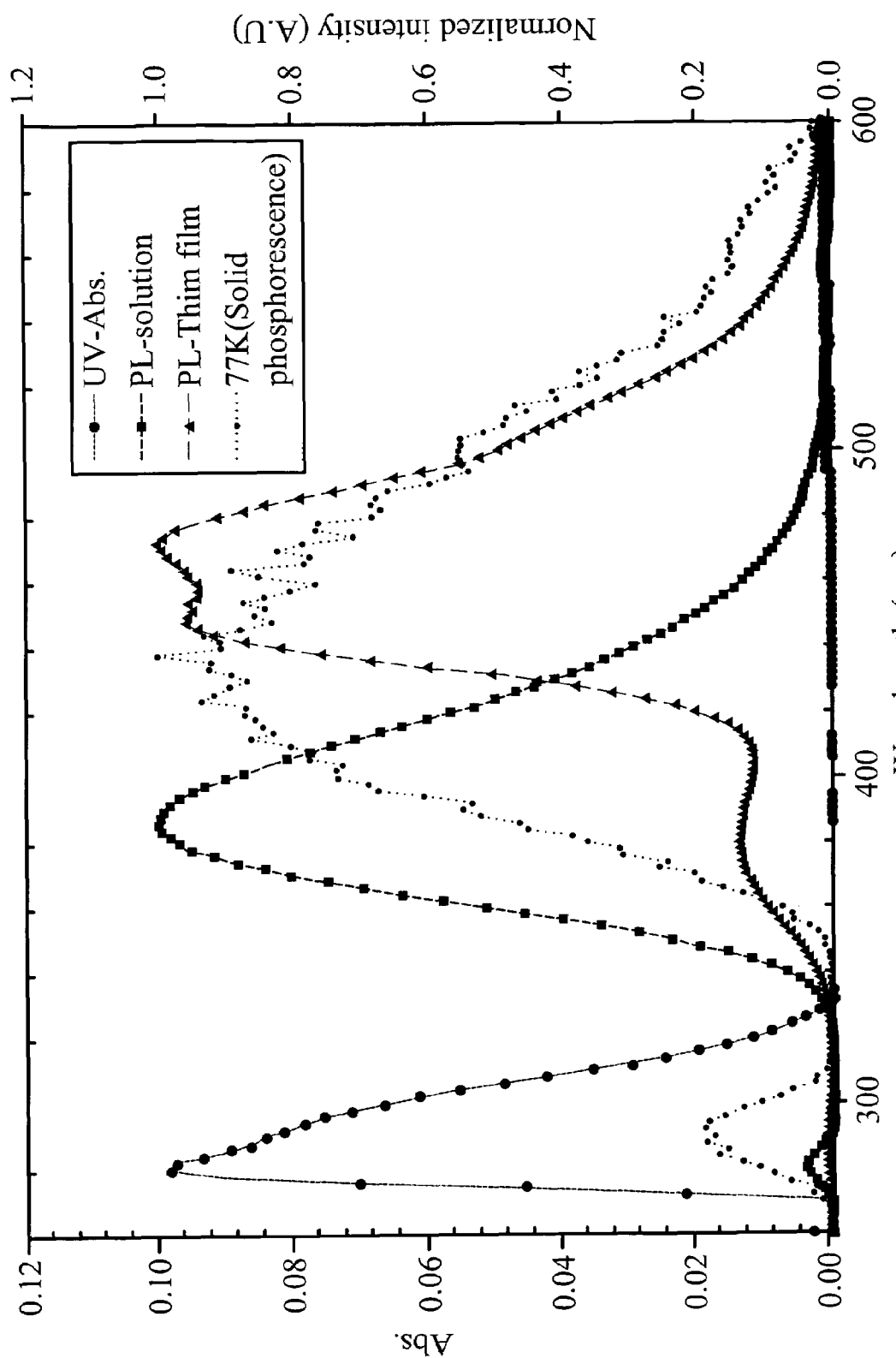
FIG. 8 shows UV-VIS absorption and photo luminescent spectra of the TTA-BP in a dichloromethane solution and thin film type, and solid phosphorescence emission spectra at 77K of the TTA-BP.

Synthesis of 2,3,6,7-Tetrakis-biphenyl-4-yl-9,9,10,10-tetramethyl-9,10-dihydro-anthracene Similar to Example 3, the only difference was that the 4-tert-butylphenylboronic acid in Example 3 was replaced with biphenylboronic acid, while other reaction reagents, steps, and conditions were the same. The product of Example 7 has a formula as shown in Formula 11, named 2,3,6,7-Tetrakis-biphenyl-4-yl-9,9,10,10-tetramethyl-9,10-dihydro-anthracene (hereinafter TTA-BP). TTA-BP had a specta as below. $^1$H NMR (400 M Hz, CDCl$_3$): δ 1.86 (s, 12 H), 7.31-7.33 (m, 12 H), 7.39-7.43 (m, 8 H), 7.51 (d, 8 H, J=7.2 Hz), 7.60 (d, 8 H, J=7.2 Hz). HRMS (FAB, m/z): calcd for C$_{66}$H$_{52}$ 844.4069, found 845.4141 (M+H$^+$). FIG. 8 shows UV-VIS absorption and photo luminescent spectra of the TTA-BP in a dichloromethane solution and thin film type, and solid phosphorescence emission spectra at 77K of the TTA-BP.

(Formula 11)

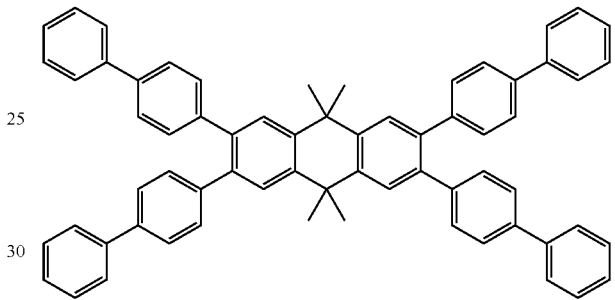

EXAMPLE 8

Manufacturing a Blue OLED

The products of Examples 3-6 (host material) were evenly mixed with FIrpytz (dopant) in volume ratio of 94:6 to be light emitting materials, respectively.

Figure 9:
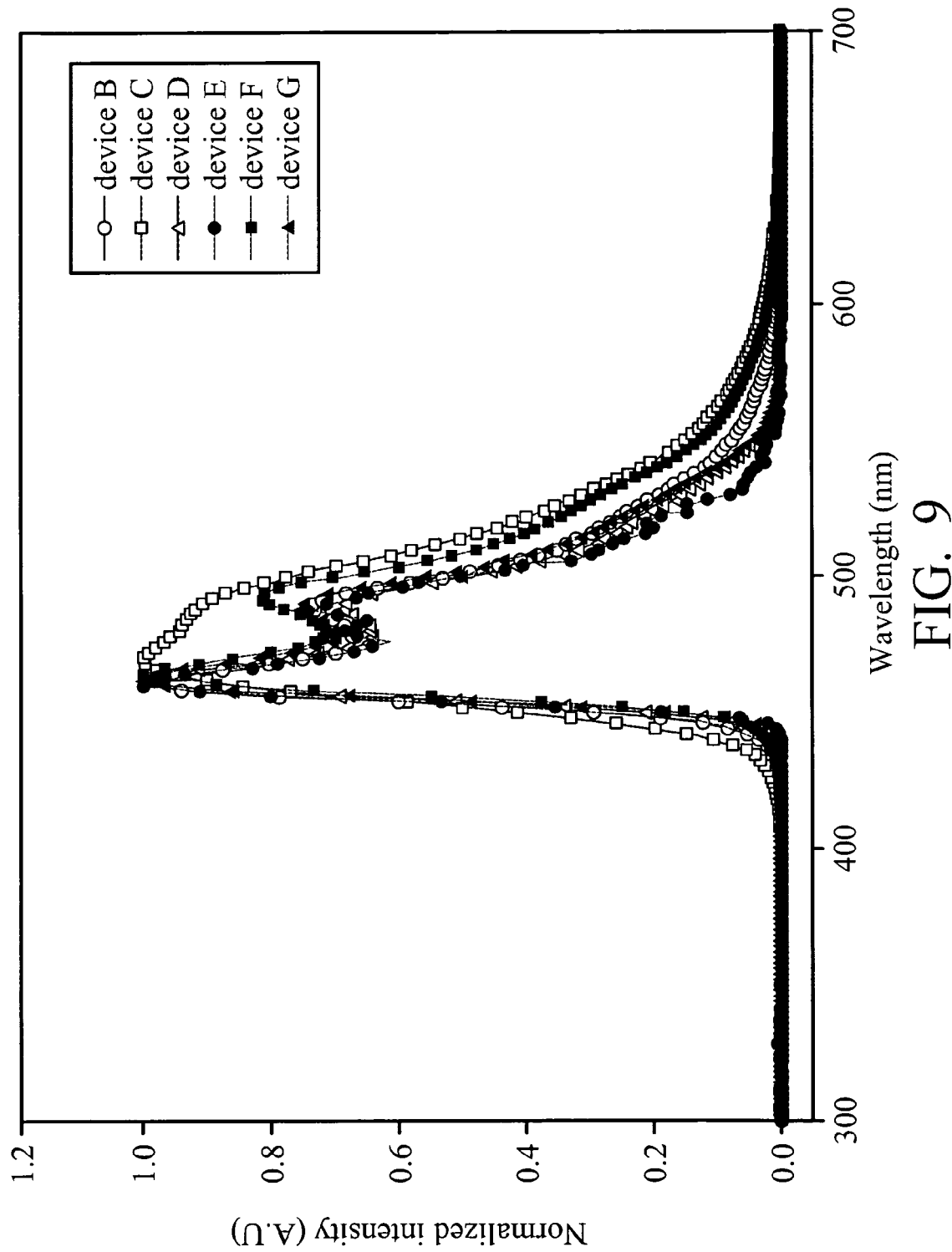
FIG. 9 shows the emission spectra of devices B-G.

As shown in FIG. 1, ITO was formed on the glass substrate 11, washed by wet etching or plasma to form an anode 12 with 80 nm thickness. NPB was then evaporated on the anode 12 to form a HTL 13 with 30 nm thickness. mCP was then evaporated on the HTL 13 to form an EBL 14 with 20 nm thickness. The described light emitting material was then evaporated on the EBL 14 to form a light emitting layer 15 with 30 nm thickness. BCP was then evaporated on the light emitting layer 15 to form a HBL 16 with 10 nm thickness. Alq$_3$ was then evaporated on the HBL 16 to form an ETL 17 with 30 nm thickness. Finally, magnesium-silver alloy was vacuum coated on the ETL 17 to form a cathode 18 with 55 nm thickness. The materials of every layer of the blue OLED are shown in Table 1, the emission efficiency of every device are shown in Table 2, and the emission spectra of devices B-G are shown as FIG. 9, respectively.

TABLE 1

| | Device | | | | | | |
|---|---|---|---|---|---|---|---|
| | A | B | C | D | E | F | G |
| Anode | | | | ITO | | | |
| HTL | NPB | NPB | NPB | NPB | TCTA | TCTA | TCTA |
| EBL | | | | mCP | | | |

TABLE 1-continued

| | Device | | | | | | |
|---|---|---|---|---|---|---|---|
| | A | B | C | D | E | F | G |
| Host material of light emitting layer | TTA-tBu | TTA-CF$_3$ | TTA-Me | TTA-OMe | TTA-CF$_3$ | TTA-Me | TTA-OMe |
| Dopant of light emitting layer | | | | FIrpytz | | | |
| HBL | | | | BCP | | | |
| ETL | | | | Alq$_3$ | | | |
| cathode | | | | Mg:Ag | | | |

TABLE 2

| device | Host material | Drive voltage (V) | External quantum efficiency (%, V) | Brightness at 100 mA/cm$^2$ (Cd/m$^2$) | Current efficiency (Cd/A, V) | Power efficiency (lm/W, V) | CIE Coordinates (x, y) at 10 V |
|---|---|---|---|---|---|---|---|
| A | TTA-tBu | 6.1 | 1.53, 13.0 | weak | 2.44, 13.0 | 0.61, 12.5 | 0.14, 0.21 |
| B | TTA-CF$_3$ | 5.2 | 6.60, 9.0 | 1158 | 10.83, 9.0 | 4.03, 8.0 | 0.13, 0.21 |
| C | TTA-Me | 6.1 | 4.95, 11.0 | weak | 8.73, 11.0 | 2.58, 10.0 | 0.14, 0.26 |
| D | TTA-OMe | 5.1 | 5.20, 8.5 | 4006 | 8.58, 8.5 | 3.24, 8.0 | 0.12, 0.19 |
| E | TTA-CF$_3$ | 3.7 | 4.34, 7.0 | 2034 | 9.59, 7.0 | 4.31, 7.0 | 0.11, 0.17 |
| F | TTA-Me | 7.5 | 2.73, 14.5 | 3569 | 5.30, 14.5 | 1.14, 14.5 | 0.14, 0.27 |
| G | TTA-OMe | 4.1 | 5.69, 7.0 | 5994 | 9.85, 7.0 | 4.67, 6.5 | 0.11, 0.21 |

Referring to Table 2, the 2,3,6,7-tetraryl-9,9,10,10-tetramethyl-9,10-dihydro-anthracenes can serve as a host material utilized in a light emitting layer of the OLED. The device utilizing the host material of the invention may emit blue phosphorescence with high brightness, high current efficiency, and excellent CIE coordinate.

While the invention has been described by way of example and in terms of preferred embodiment, it is to be understood that the invention is not limited thereto. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A host material, having a general formula:

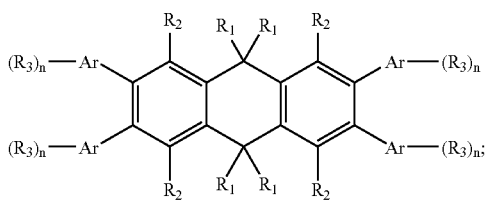

wherein $R_1$ is selected from a $C_{1-8}$ alkyl group;
each $R_2$ is independently selected from a hydrogen or a $C_{1-8}$ alkyl group;
Ar is selected from a $C_{5-14}$ aromatic or hetero aromatic group;
$R_3$ is selected from a $C_{5-14}$ aromatic or hetero aromatic group, a $C_{1-8}$ alkyl group, a $C_{5-8}$ cycloalkyl group, a $C_{1-8}$ fluoroalkyl group, or a $C_{1-8}$ alkoxyl group; and
n is an integer of 1-10.

2. The host material as claimed in claim 1, wherein $R_1$ is methyl and $R_2$ is hydrogen.

3. The host material as claimed in claim 1, wherein Ar is a phenyl group, n is 2, and $R_3$ are in meta positions of the phenyl group.

4. The host material as claimed in claim 1, wherein Ar is a phenyl group, n is 1, and $R_3$ is in para positions of the phenyl group.

5. A blue OLED, comprising:
an anode;
a hole transporting layer on the anode;
an electron blocking layer on the hole transport layer;
a light emitting layer on the electron blocking layer;
a hole blocking layer on the light emitting layer;
an electron transporting layer on the hole blocking layer; and
a cathode;
wherein the light emitting layer comprises the host material as claimed in claim 1 and a dopant.

6. The blue OLED as claimed in claim 5, wherein the anode comprises ITO, IZO, AZO, CTO, SnO$_2$, or ZnO.

7. The blue OLED as claimed in claim 5, wherein the hole transporting layer comprises NPB, TPD, NCB, PPB, MPMP, HMTPD, or TCTA.

8. The blue OLED as claimed in claim 5, wherein the electron blocking layer comprises mCP, CBP, CCP, or TCB.

9. The blue OLED as claimed in claim 5, wherein the dopant comprises FIrpytz, FIRpic, FIRN4, FIr6, or Ir(pmb)$_3$.

10. The blue OLED as claimed in claim 5, wherein the hole blocking layer comprises TPBI, BCP, BAlq, PAlq, SAlq, or UGH2.

11. The blue OLED as claimed in claim 5, wherein the electron transporting layer comprises TPBI, TAZ-1, TAZ-2, TAZ-3, PBD, Alq$_3$, or DPA.

12. The blue OLED as claimed in claim 5, wherein the cathode comprises magnesium-aluminum alloy, magnesium-silver alloy, magnesium-indium alloy, aluminum-lithium alloy, lithium fluoride, or aluminum.

13. The blue OLED as claimed in claim 5, further comprising a hole injection layer between the anode and the hole transporting layer, and the hole injection layer comprises arylamine, porphyrin, p-doped amine, or derivatives thereof.

14. The blue OLED as claimed in claim 5, further comprising an electron injection layer between the cathode and the electron transporting layer, and the electron injection layer comprises alkali metal halides, alkaline earth metal halides, alkali metal oxide, or metal carbonate.

15. A white light emitting device, comprising:
the blue OLED as claimed in claim 5;
a red OLED; and
a green OLED.

* * * * *